United States Patent [19]
Leahy et al.

[11] Patent Number: 5,813,409
[45] Date of Patent: Sep. 29, 1998

[54] SURGICAL APPARATUS

[75] Inventors: Patrick F. Leahy, Blackrock, Ireland; Berwyn M. Crook, Yardley; Robert D. Rambo, Sellersville, both of Pa.

[73] Assignee: Medical Creative Technologies, Inc., Colmar, Pa.

[21] Appl. No.: 410,316

[22] Filed: Mar. 29, 1995

Related U.S. Application Data

[63] Continuation-in-part of Ser. No. 300,346, Sep. 2, 1994, Pat. No. 5,640,977.

[51] Int. Cl.$^6$ .................................................. A61B 19/00
[52] U.S. Cl. ......................... 128/897; 128/850; 606/215; 604/174
[58] Field of Search .................. 600/21–22; 128/897, 128/846, 850–56; 604/167, 174, 178, 237, 256; 606/213, 215

[56] References Cited

U.S. PATENT DOCUMENTS

| | | |
|---|---|---|
| 1,810,466 | 6/1931 | Deutsch . |
| 2,305,289 | 12/1942 | Coburg . |
| 2,835,253 | 5/1958 | Borgeson . |
| 3,111,943 | 11/1963 | Orndorff . |
| 3,244,169 | 4/1966 | Baxter . |
| 3,332,417 | 7/1967 | Blandford et al. . |
| 3,347,226 | 10/1967 | Harrower . |
| 3,347,227 | 10/1967 | Harrower . |
| 3,397,692 | 8/1968 | Creager et al. . |
| 3,416,520 | 12/1968 | Creager, Jr. . |
| 3,523,534 | 8/1970 | Nolan . |
| 3,841,332 | 10/1974 | Treacle . |
| 3,850,172 | 11/1974 | Cazalis . |
| 4,024,872 | 5/1977 | Muldoon . |
| 4,043,328 | 8/1977 | Cawood et al. . |
| 4,188,945 | 2/1980 | Wenander . |
| 4,367,728 | 1/1983 | Mutke . |
| 4,550,713 | 11/1985 | Hyman . |
| 4,553,537 | 11/1985 | Rosenberg . |
| 4,777,943 | 10/1988 | Chvapil . |
| 4,903,710 | 2/1990 | Jessamine et al. . |
| 4,926,882 | 5/1990 | Lawrence . |
| 4,991,593 | 2/1991 | LeVahn . |
| 4,998,538 | 3/1991 | Charowsky et al. . |
| 5,037,379 | 8/1991 | Clayman et al. . |
| 5,178,162 | 1/1993 | Bose . |
| 5,299,582 | 4/1994 | Potts . |
| 5,316,541 | 5/1994 | Fischer . |
| 5,653,705 | 8/1997 | de la Torre et al. . |
| 5,672,168 | 9/1997 | de la Torre et al. . |

FOREIGN PATENT DOCUMENTS

WO 95/24864   9/1995   WIPO .

*Primary Examiner*—John P. Lacyk
*Attorney, Agent, or Firm*—Howson and Howson

[57] ABSTRACT

An improved surgical apparatus for hand-assisted minimum invasive surgery with isolation at the site of a wound from ambient conditions. A sleeve of gas-impermeable material includes entry and exit openings for access to the wound, and ports for introducing surgical instruments into the sleeve within easy reach of a surgeon's hand.

40 Claims, 5 Drawing Sheets ic apparatus

SURGICAL APPARATUS

CROSS-REFERENCE TO RELATED APPLICATION

This application is a continuation-in-part of U.S. patent application Ser. No. 08/300,346 filed Sep. 2, 1994, now U.S. Pat. No. 5,640,977 issued Jun. 24, 1997.

FIELD OF INVENTION

The present invention relates generally to apparatus for use in surgery, and more particularly to improvements in surgical apparatus suitable for maintaining a sterile aseptic environment while performing open or minimum invasive surgery.

BACKGROUND OF THE INVENTION

Laparoscopic surgery has become a procedure of choice for certain abdominal operations because of the relatively small incisions involved and the minimal trauma and shortened healing time for the patient. However, not all surgeons have the highly specialized training and experience needed to perform the required critical surgical tasks with trocar and cannula assemblies while observing a remote TV image of the abdominal cavity under conditions of pneumoperitoneum.

A modified or hybrid form of laparoscopic surgery, more adaptable to surgeons trained only in conventional surgical techniques, is now possible with a surgical apparatus especially developed for hand-assisted minimum invasive laparoscopic surgery while still maintaining pneumoperitoneum. The mere presence of one hand of the surgeon in the abdominal cavity together with a laparoscope enables the trocar and cannula assemblies to be precisely and safely moved about by feel as well as by sight on a TV monitor.

Such an apparatus is disclosed in pending U.S. patent application Ser. No. 08/300,346 filed Sep. 2, 1994 by the inventors of the present invention. A flexible sleeve with an entry opening at the proximal end is sealed by an adjustable cuff around the surgeon's forearm when his/her hand is inserted into the sleeve, and an exit opening on one side near the distal end of the sleeve is sealed by an adhesive flange around an incision through which the surgeon's hand may pass into the abdominal cavity. A duckbill check valve located between the entry and exit openings defines an antechamber along the forearm which prevents loss of pneumoperitoneum while the hand is being inserted or removed from the sleeve during a surgical procedure such as when retrieving various surgical instruments.

However, the apparatus does not permit the surgeon or other operating room personnel to introduce or remove instruments directly into the sleeve at the site of the incision during an operation, or to store these instruments within the sleeve where they can be easily grasped by the surgeon; nor will the apparatus enable the surgeon to use both hands, or the hand of an assistant, within the sleeve.

Furthermore, brief interruptions in the course of an operation may not be feasible where the surgeon needs to withdraw his/her arm from the sleeve from time to time.

SUMMARY OF THE INVENTION

Accordingly, it is an object of the present invention to provide a surgical apparatus suitable for open or minimum invasive surgery while maintaining a sterile aseptic environment at the operating site.

Another object of the invention is to provide a gas-impervious sleeve for hand-assisted surgery in which conventional instruments can be inserted under conditions of pneumoperitoneum within easy reach of the surgeon's hand.

Still another object of the invention is to provide a surgical apparatus which is suitable for hand-assisted surgery under conditions of pneumoperitoneum, and which can be quickly disconnected and reconnected around the site of an incision to accommodate brief interruptions in the course of an operation.

A still further object of the invention is to provide a surgical apparatus suitable for maintaining a sterile aseptic environment in the immediate vicinity of a wound during a surgical procedure initiated under emergency conditions at a field station and subsequently while the patient is being transported to a more fully equipped aseptic operating room environment where the surgical procedure can be completed.

These and other objects and novel features of the invention are accomplished with a surgical apparatus in which a flexible sleeve includes an exit opening near a distal end for adhesively sealing around an incision in a patient, and sealable hand and instrument entry openings for maintaining an isolated and aseptic environment in the immediate vicinity of the incision. One preferred embodiment includes access ports with duckbill check valves in the sleeve near the incision which allow laparoscopic and other surgical instruments to be introduced or removed from the sleeve without losing pneumoperitoneum or sterile integrity at the site. In a second embodiment, two sleeves communicate with a transparent dome-shaped envelope for receiving both hands. The envelope is completely closed except for an opening in the bottom side which adhesively seals to the patient around the operating site, and access ports with duckbill check valves extending into the top of the envelope for instruments to be passed in and out during surgery. A third embodiment includes a short sleeve with a quick-disconnect ring and an adhesive flange at a distal end opening which seal around the outer end of a wound protector emplaced in the incision. A cuff at the proximal end opening seals the sleeve around the arm of the surgeon, and instrument access ports with duckbill check valves maintain pneumoperitoneum and sterile integrity at the incision while the sleeve is connected to the wound protector during surgery.

BRIEF DESCRIPTION OF THE DRAWINGS

The foregoing and other objects, novel features, and advantages of the invention will become more apparent from the following description when taken in conjunction with accompanying drawings wherein.

DESCRIPTION OF THE PREFERRED EMBODIMENTS

Figure 1:
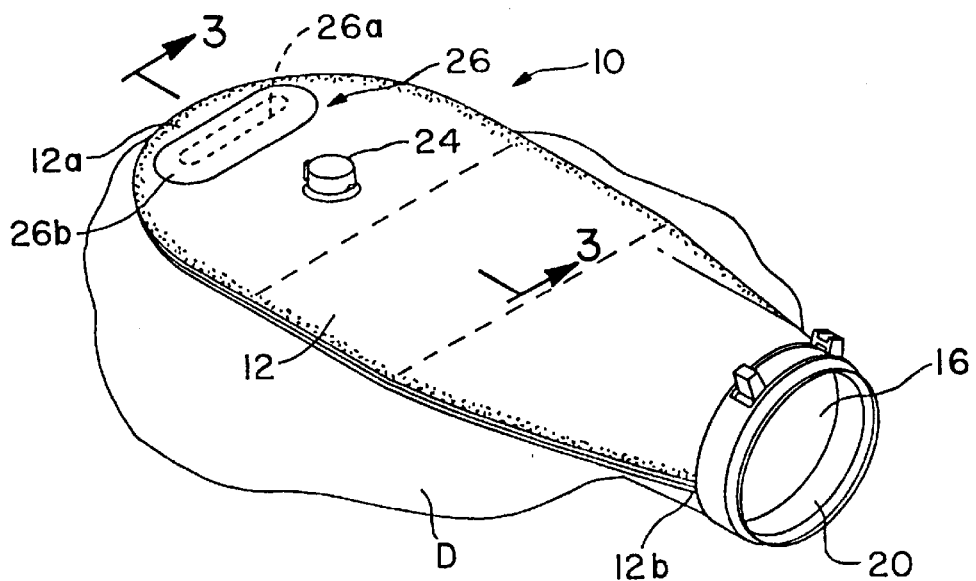
FIG. 1 is a perspective view of one preferred embodiment of a surgical apparatus according to the invention suitable for minimum invasive abdominal surgery.
Figure 3:
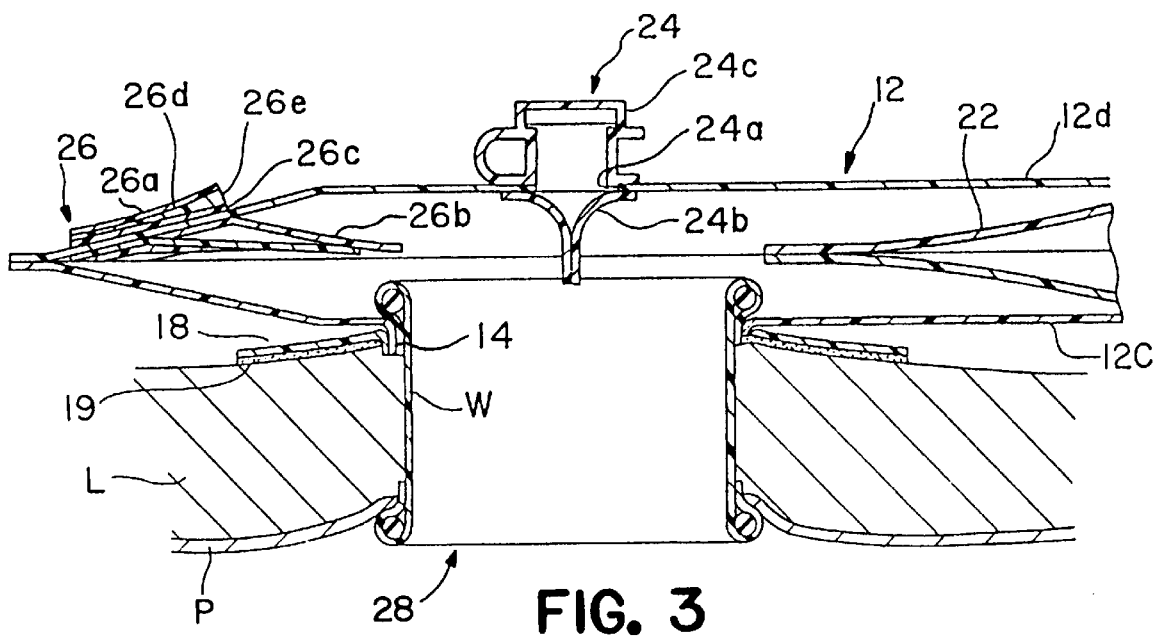
FIG. 3 is a longitudinal cross-sectional view of the distal end of the surgical apparatus of FIG. 1 taken along the line 3—3.
Figure 2:
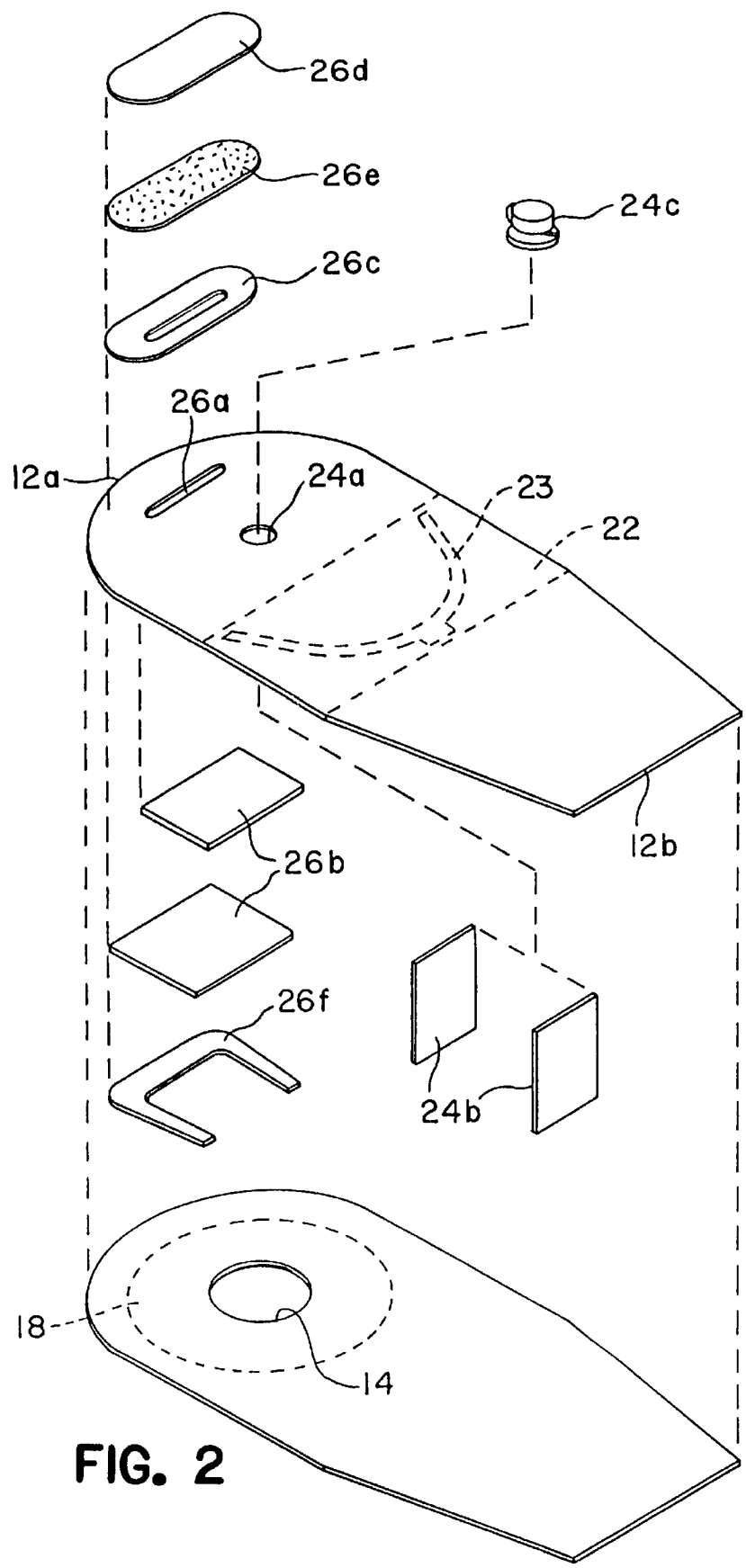
FIG. 2 is an exploded isometric view in flat layout of principal components of the surgical apparatus of FIG. 1.

Referring now to the drawings wherein like reference characters denote like or corresponding parts throughout the several views, there is shown in FIGS. 1, 2 and 3 a surgical apparatus, indicated generally by the numeral 10, adhering to a patient's abdominal wall L. Of course, if a surgical drape were first applied to the operating site, flange 18 would adhere as well to the upper surface of the drape around a wound W.

Apparatus 10 includes a gas-impermeable, flexible sleeve 12 having a distal end 12a with an exit opening 14 in a bottom panel 12c around wound W sized to pass a surgeon's hand through, and a proximal end 12b with an entry opening 16 remote from the site sized to pass the surgeon's hand through and receive the forearm. A flange 18, fixed to panel 12c around exit opening 14, is coated on the bottom exposed side with an adhesive 19 for adhering to the abdominal wall L. A release or peel-strip backing (not shown) completely covers the adhesive prior to use. A non-toxic, biocompatible adhesive found especially suitable for hypersensitive skin is an acrylate polymer, such as IT8-59-A by Tolas Health Care Packaging of Feasterville, Pa., having a thickness of 0.002 in., peel adhesion 8 to 10 lb/sq. in., shear resistance of 1.2 hrs. at 1 kg/sq.in., and tack 1250 g/sq. cm. around wound W. An adjustable cuff 20 in entry opening 16 clamps around the forearm to form a chamber in sleeve 12 communicating with the abdominal cavity. An inner gas-lock or duckbill check valve 22 biased normally closed by a bias stay 23, defines an antechamber in sleeve 12 with cuff 20 around the surgeon's arm to minimize loss of insufflation under conditions of pneumoperitoneum when cuff 20 is breached. Sleeve 12, valve 22 and cuff 20 are preferably constructed of 3-mil polyolefin with flange 18 of 4-mil polyolefin materials and in the manner such as disclosed in patent application Ser. No. 08/300,346, supra, the disclosure of which is incorporated by reference herein.

Access ports 24 and 26, located near exit opening 14 in a top panel 12d of sleeve 12 allow instruments or the like to be inserted during surgery while maintaining pneumoperitoneum. As best seen in FIG. 2, port 24 defines an opening 24a located approximately coaxial with exit opening 14 and includes a duckbill check valve 24b extending into sleeve 12. An external snap-on cap 24c covers opening 24a when not in use. Access port 26 defines a slot 26a transverse to the length of sleeve 12 between port 24 and distal end 12a and includes a duckbill check valve 26b extending into sleeve 12. A grommet 26c fixed around slot 26a provides stiffening and tear resistance, and a strip 26d coated on one side with a peelable adhesive 26e sealingly adheres to the exposed surface of grommet 26c. On account of the width of duckbill check valve 26a, tension is applied between the opposite sides thereof by a U-shaped stay 26f made of a thin strip of resilient material, such as a high density polyethylene plastic, in order to maintain valve 26a in a normally closed position. Port 24 is sized to pass slender instruments such as lumens and trocars, whereas port 26 is sized to pass wider instruments such as clamps and forceps. The duckbill configuration of the check valve 24 and 26 comprises two flexible flat panels joined to each other on opposite sides and around the respective specimens 24a and 26a.

A wound protector 28, such as disclosed in patent application Ser. No. 8/300,346, supra, and incorporated by reference herein emplaced in exit opening 16 and extending through abdominal wall L and peritoneum P, protects wound W from exposure to diseased tissue and non-sterile material passing through the wound during surgery.

Figure 4:
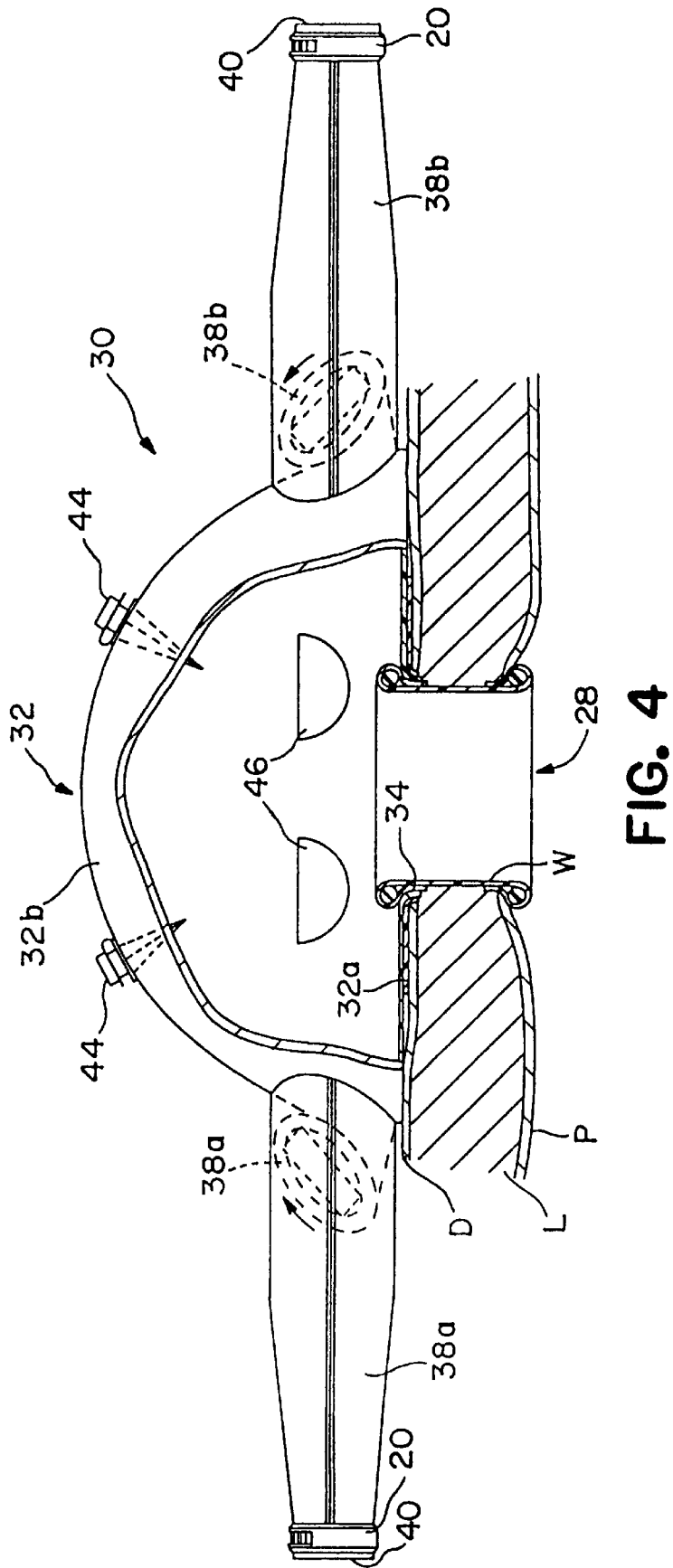
FIG. 4 is a view partially in cross-section of another preferred embodiment of the surgical apparatus according to the invention which is especially suitable for use with both hands or under emergency field conditions.

Referring now to FIG. 4, there is shown a surgical apparatus, indicated generally by the numeral 30, which is especially suitable for obtaining an aseptic environment in the immediate vicinity of wound W for performing emergency abdominal surgery such as at a mobile field hospital. Apparatus 30 comprises a flexible enclosure 32 made of a generally flat bottom panel 32a covered by a dome-shaped top panel 32b. An exit opening 34 in bottom panel 32a includes an adhesive flange for sealing to surgical drape D around an aforedescribed wound protector 28 emplaced in wound W. A distal end of flexible left and right sleeves 38a and 38b, respectively, communicate with the interior of enclosure 32 through openings in top panel 32b on generally opposite sides thereof. Entry openings 40 at proximal ends of sleeves 38a and 38b each includes an aforedescribed adjustable cuff 20 which tightens around the surgeon's forearms and completely isolates wound W from ambient conditions.

Top panel 32b of enclosure 32 includes access ports 44 constructed like access port 24 of FIG. 2 for passing instruments through to the surgeon. The size of the port is determined according to the size and shape of the instruments. In addition, pockets 46 affixed to the interior of top panel 32b are provided for storing instruments and other devices at easily accessible locations. The shape of the pockets depend on the type of device stored.

Top panel 32b is preferably made of a thin transparent plastic film to give the surgeon a clear view of the operating site. Apparatus 30 being made of flexible material allows the surgeon in a field emergency situation to close wound W temporarily and roll up sleeves 38a and 38b, as shown in broken outline, thereby sealing enclosure 32 for transporting the patient to another facility with apparatus 30 attached where the surgery can be completed under better conditions. Elastic bands or clips, not shown, may be applied to keep the sleeves from unrolling.

Figure 5:
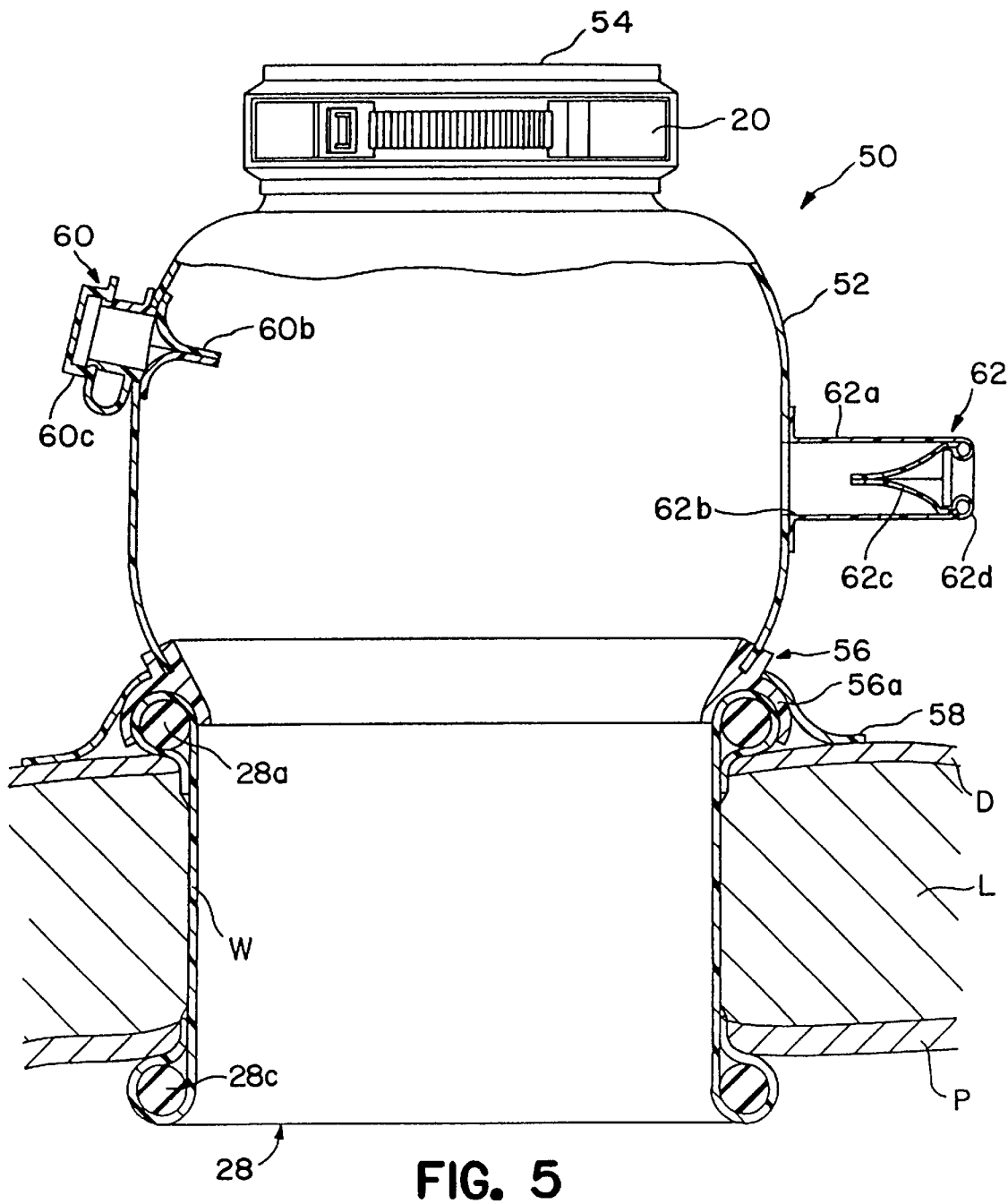
FIG. 5 is a view partially in cross-section of still another preferred embodiment of the surgical apparatus according to the invention having a quick-disconnect sleeve.

Referring now to FIG. 5, there is shown a surgical apparatus, indicated generally by the numeral 50, for hand-assisted minimum invasive surgery under conditions of pneumopentoneum which can be readily connected and disconnected by the surgeon during the operation. Apparatus 50 comprises a sleeve 52 having an entry opening 54 at a proximal end which is tightened around a surgeon's forearm by an adjustable cuff 20 as described in FIG. 1. An elastic ring 56 at the distal end of sleeve 52 defines an annular lip 56a with an interference fit with an exposed O-ring 28a of a wound protector 28 which has been emplaced in wound W in the manner described in patent application Ser. No. 08/300,346, supra, the disclosure of which is incorporated by reference herein. Protector 28 includes a flexible tube 28b secured around one end of O-ring 28a and around an O-ring 28c at the opposite end. An adhesive-coated flange 58 about ring 56 adheres to surgical drape D to sealingly enclose sleeve 52 about the wound.

Ports 60 and 62 provide direct access for instruments to be inserted into sleeve 52 without losing insufflation pressure, if any is present. Port 60 is constructed with check valves 60b and snap-on cap 60c in the same manner as port 24 of FIG. 1. Port 62 is preferably constructed of a semi-rigid sleeve 62a communicating at one end through an opening 62b in sleeve 52. A duckbill valve 62c extends toward opening 62b from an O-ring 62d secured around the other end of sleeve 62a.

The method of using the several disclosed embodiments of the surgical apparatus are similar. Basically, the abdomen is routinely prepared with anteseptics and dried, and an incise drape D is applied to the operating site. An incision with a scalpel is made at the site of sufficient size for a surgeon's hand to pass through. A wound protector 28 corresponding in size with the incision is placed in the wound by squeezing one O-ring into a tight ellipse and inserting it lengthwise through the incision until it expands inside the peritoneum and the O-ring on the other end overlaps the exposed drape D around wound W. With the surgeon's hand extending into the abdominal cavity through the wound protector 28, trocars/cannulas may be guided into place and the hand removed in order to attach one of the above-described surgical apparatus 10, 30, or 50. The hand is then reinserted through the openings of the apparatus for drawing outer O-ring through opening 14 and allowing it to expand inside sleeve 12 around the opening, and the cavity insufflated. Instruments and other materials may then be inserted within easy reach of the surgeon's hand through the various ports, or may be stored in pockets within the apparatus.

Figure 7:
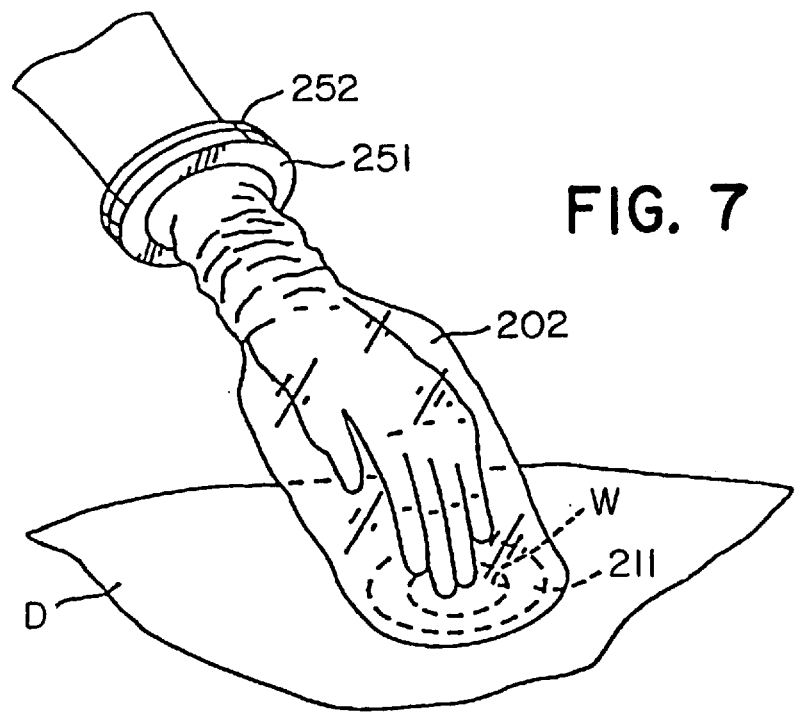
FIG. 7 is a view showing the FIG. 6 embodiment in use.
Figure 6:
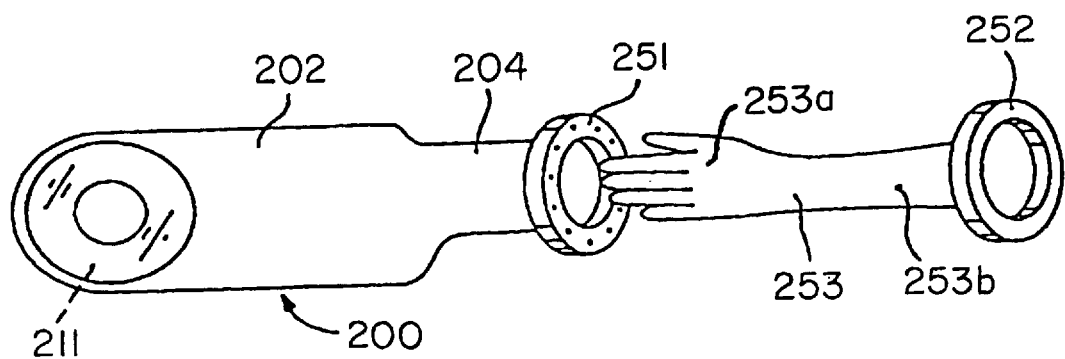
FIG. 6 is an exploded perspective view of another embodiment of the invention.

Another simplified embodiment is illustrated in FIG. 6. As seen therein, a surgical apparatus 200 similar in construction to apparatus 100 of FIGS. 3–17 in Applicants' incorporated by reference copending application Ser. No. 300,346, now U.S. Pat. No. 5,640,977 is provided, except that a first flange 251 is integral with a proximal end 204 of a sleeve 202, and a second flange member 252 is integral with a surgeon's glove 253 having a hand and finger receiving portion 253*a* and an elongate gauntlet portion 253*b* mounting the second flange 252 in the region of the open end thereof. When the surgeon's arm with glove 253 passes into sleeve 202, flanges 251 and 252 are sealingly interengaged. FIG. 7 illustrates the embodiment of FIG. 6 in use in surgery. As seen therein, the inner glove 253 extends interiorily of the sleeve 202 and is connected thereto at the sleeve proximal end 204 to afford a range of arm movement of the surgeon relative to the patient under insufflation conditions of the patients's cavity. An adhesive coated ring 211, as described heretofore, and in the parent application, extends around the wound W for effecting a sealed gastight connection of the outer sleeve 202 onto the patient over which a conventional surgical drape D is installed.

Some of the many advantages and novel features of the invention should now be readily apparent. For example, a surgical apparatus is provided which is especially suitable for open or minimum invasive surgery while maintaining a sterile aseptic environment at the operating site. Ports with duckbill check valves are provided in the apparatus which allow instruments of various shapes and sizes to be inserted under conditions of pneumoperitoneum and within easy reach of the surgeon's hand. The apparatus can be quickly disconnected and reconnected around the site of an incision to accommodate brief interruptions in the course of an operation. In one of the disclosed embodiments, the apparatus can remain attached to the patient while being transferred from a field hospital to a more complete operating room facility where the surgery can be completed.

It will be understood, of course, that various changes in the details, materials, steps and arrangement of parts, which have been herein described and illustrated in order to explain the nature of the invention may be made by those skilled in the art within the principal and scope of the invention as expressed in the appended claims.

It is claimed:

1. An improved surgical apparatus for hand-assisted minimum invasive surgery with isolation at the site of a wound from ambient conditions, said apparatus including a sleeve of gas-impermeable supple material having an entry opening at a proximal end thereof and an exit opening at a distal end thereof, first sealing means adapted to seal the exit opening around the wound, and second sealing means adapted to seal the entry opening around a surgeon's forearm to create a gastight chamber in said sleeve, the improvement comprising:

at least one port means in said sleeve proximal to said exit opening formed to maintain effective isolation of the wound while passing surgical instruments through said port means into said chamber.

2. The improvement according to claim 1 wherein:

said port means includes a first aperture disposed in said sleeve oppositely from said exit opening, and a first duckbill check valve connected to said sleeve for communicating between said first aperture and said chamber.

3. The improvement according to claim 2 further comprising:

a snap-on cap means connected to said port means for manually closing said first aperture.

4. The improvement according to claim 2 wherein:

said first check valve is formed to pass lengthwise slender surgical instruments, including trocars and lumens.

5. The improvement according to claim 2 wherein:

said port means includes an elongate second aperture disposed in said sleeve near the distal end and athwart the length thereof, and a second duckbill check valve connected to said sleeve for communicating between said second aperture and said chamber.

6. The improvement according to claim 5 further comprising:

grommet means lining said second aperture for providing stiffness and tear resistance thereto, and a peelable strip adhesively secured to an exposed surface of said grommet for manually closing said second aperture to the ambient conditions.

7. Apparatus according to claim 5 wherein:

said second check valve is formed to pass lengthwise wide instruments, including forceps and clamps.

8. The improvement according to claim 5 wherein:

said first and second check valves each comprise two flexible panels with opposite congruent side edges respectively joined together, and one end of said panels joined to said sleeve around respective ones of said apertures.

9. The improvement according to claim 1 wherein:

said port means includes a plurality of apertures in said sleeve disposed in close proximity to said exit opening, and a duckbill check valve at each of said apertures connected to said sleeve and communicating between each of said apertures and said chamber.

10. The improvement according to claim 1 further comprising:

an adhesive coating secured to the first sealing means for adhering around the wound comprises an acrylate polymer of about 0.002 in. thickness, approximate physical properties of peel adhesion 8 to 10 $lb/in^2$, shear resistance of 1.2 hrs. at 1 $kg/in^2$, and tack 1250 $g/cm^2$.

11. Apparatus for enabling surgery with two hands with isolation at the site of a wound from ambient conditions comprising, in combination:

a dome-shaped gas-impermeable enclosure having a centrally disposed exit opening adapted to seal around the wound; and at least two gas-impermeable sleeves, each sleeve communicating at a distal end thereof through an opening with the interior of said enclosure, and an entry opening at a proximal end thereof adapted to seal about the forearm of a hand extended therein forming thereby a gas-tight chamber with said enclosure.

12. Apparatus according to claim 11 further comprising:

at least one port means formed in said enclosure proximal to said exit opening for effectively maintaining isolation while passing surgical instruments through said port means into said chamber.

13. Apparatus according to claim 12 wherein:

said port means includes an aperture disposed in said enclosure, and a check valve connected to said enclosure for communicating between said aperture and said chamber.

14. Apparatus according to claim 13 wherein:

said check valve is formed to pass surgical instruments through.

15. Apparatus according to claim 13 further comprising:

a snap-on cap connected to said port means for manually closing said aperture.

16. An improved surgical apparatus for hand-assisted surgery with isolation at the site of a wound from ambient conditions, said apparatus including a sleeve of gas-impermeable supple material having an entry opening at a proximal end thereof and an exit opening at a distal end thereof, first sealing means adapted to seal the exit opening around the wound, and second sealing means adapted to seal the entry opening around a surgeon's forearm to create a gastight chamber in said sleeve, the improvement comprising:

a wound protector including a flexible tube adapted to line the wound, said tube having resilient rings at respective ends thereof, for stretching the ends of said tube around the internal and external surfaces of the wound; and an annular lip formed at the distal end of said sleeve having an interference fit formed to snap onto said ring at the external end of said tube.

17. The improvement according to claim 16 further comprising:

a flexible flange recessed around said lip and having an exposed face for adapted to attach around the site of the wound.

18. The improvement according to claim 16 further comprising:

at least one port means formed in said sleeve proximal to said exit opening for effectively maintaining isolation while passing surgical instruments through said port means into said chamber near the site of the wound.

19. The improvement according to claim 18 wherein:

said port means includes an aperture disposed in said sleeve oppositely from said exit opening, and a duckbill check valve connected to said sleeve for communicating between said aperture and said chamber.

20. The improvement according to claim 18 further comprising:

a snap-on cap means connected to said port means for manually closing said aperture.

21. The improvement according to claim 19 wherein:

said check valve is formed to pass lengthwise slender surgical instruments, including trocars and lumens.

22. A method for hand-assisted minimum invasive surgery with isolation at the site of a wound from ambient conditions, the method comprising:

providing a gas-impermeable sleeve having an entry opening at a proximal end adapted to seal around a surgeon's forearm, an exit opening at a distal end for fenestration with the wound, and at least one surgical instrument access port near the distal end;

adhering the sleeve at the exit opening around the wound;

inserting a hand in the sleeve through the entry and exit openings to the wound; and introducing surgical instruments into the sleeve through the access port to the surgeon.

23. A method according to claim 22 further comprising:

insufflating a cavity at the wound before inserting the hand or instruments into the sleeve.

24. An improved surgical apparatus for hand-assisted surgery with isolation at the site of a wound from ambient conditions, comprising:

a sleeve of gas-impermeable supple material having an entry opening at a proximal end thereof and an exit at a distal end thereof;

first sealing means formed to seal the exit opening around the wound, said first sealing means including a first resilient ring formed to be externally secured around the site of the wound, and a second resilient ring around the distal end of said sleeve having an interference fit formed to snap together with said first ring; and second sealing means formed to seal the entry opening around the surgeon's forearm to create a gastight chamber in said sleeve.

25. An apparatus according to claim 24 wherein:

said first ring includes an continuous rib; and said second ring includes a continuous groove complementary to said rib.

26. Apparatus according to claim 24 further comprising:

a flexible tube secured around one end thereof to said first ring for lining the wound; and a resilient internal ring fixed to said tube around the other end thereof for stretching said tube around the internal surface of the wound.

27. Apparatus for use on a patient undergoing endoscopic surgery, said apparatus comprising:

a flexible envelope providing a chamber surrounding an incision in the patient, said envelope having a port affording access into said chamber from outside said envelope;

a normally-closed check valve in communication with said port to afford passage of instrumentarium into said enclosure;

a first ring gastightly secured to the patient around the incision;

a second ring gastightly carried on the enclosure; and complementary matingly engageable means on said first and second rings for effecting a releasable connection of said rings and hence the enclosure to the patient;

whereby the enclosure may be readily mounted to and dismounted from the patient.

28. Apparatus according to claim 27 wherein said check valve opens laterally into said enclosure upon admission of an instrument.

29. Apparatus according to claim 27 wherein said check valve is of the duckbill type which closes upon pressure in said chamber greater than pressure outside said chamber.

30. Apparatus according to claim 27 including a tethered cap on the outside of said envelope providing a closure for said check valve.

31. Apparatus according to claim 27 wherein said envelope has a normally open proximal end for receiving a surgeon's hand.

32. Apparatus for use on a patient undergoing endoscopic surgery, said apparatus comprising:
   a flexible enclosure having a distal end with a large opening disposable adjacent to the patient for surrounding an incision therein, said flexible enclosure having a plurality of at least three other openings spaced from said large opening, at least one of said other openings being larger than the others of said other openings;
   means for gastightly securing said envelope distal end to said patient around the outside of said incision; and
   means carried by said enclosure for operatively closing said other openings to maintain insufflation gas within the enclosure during surgery.

33. Apparatus according to claim 32 wherein said envelope securing means includes:
   a first ring gastightly secured to the patient around the incision;
   a second ring gastightly carried on the distal end of the enclosure; and
   complementary matingly engageable means on said first and second rings for effecting a releasable connection of said rings and hence the enclosure to the patient;
   whereby the enclosure may be readily mounted to and dismounted from the patient.

34. Apparatus according to claim 32 wherein at least one of said other openings includes a normally-closed duckbill check valve operable upon insertion of an instrument into the enclosure to provide a slidable seal relative to the instrument.

35. Apparatus for use in endoscopic surgery to provide a chamber above an incision in a patient, comprising:
   a flexible hemispheric enclosure having a distal end opening and at least one lateral opening spaced from said distal end opening,
   means for releasably gastightly adhesively securing said enclosure distal end outside of the patient around the incision, and
   a duckbill check valve normally closing said lateral opening while affording sliding sealed engagement with a surgical instrument.

36. Apparatus for use in minimally invasive surgery through a wound into an insufflated patient cavity, comprising:
   an outer sleeve having a distal end adapted to be positioned adjacent the patient;
   an annular ring operatively connected to said sleeve distal end for extending around the wound and effecting a sealed gastight connection of said outer sleeve onto said patient;
   an inner glove extending interiorly of said outer sleeve and connected thereto remote from said distal end for receiving a surgeon's fingers and creating a gastight chamber in said outer sleeve;
   whereby the outer sleeve cooperates with the glove to afford a range of movement during surgery under insufflation conditions of the patient's cavity.

37. Apparatus according to claim 36 wherein said inner glove has a hand receiving portion and an elongate gauntlet with an open end, and said gauntlet is connected to said sleeve.

38. Apparatus according to claim 37 wherein said gauntlet has a sealing flange around its open end for sealingly engaging said outer sleeve thereat.

39. Apparatus according to claim 36 wherein said annular ring has an adhesive layer for effecting said gastight sealed connection onto said patient.

40. Apparatus according to claim 39 wherein said adhesive is an acrylate polymer having a thickness of about 0.002 in., a peel adhesion of between about 8 to about 10 psi., a shear resistance of 1.2 hrs. at 1 kg/sq. in., and a tack of 1250 g/sq. cm.

* * * * *

UNITED STATES PATENT AND TRADEMARK OFFICE
CERTIFICATE OF CORRECTION

PATENT NO. : 5,813,409

DATED : September 29, 1998

INVENTOR(S) : Leahy et al.

It is certified that error appears in the above-identified patent and that said Letters Patent is hereby corrected as shown below:

Column 8, line 19, after "exit" add the word --opening--.

Signed and Sealed this

Nineteenth Day of January, 1999

Attest:

Attesting Officer

*Acting Commissioner of Patents and Trademarks*